United States Patent
Tsuzuki

(10) Patent No.: US 7,754,493 B2
(45) Date of Patent: Jul. 13, 2010

(54) METHOD FOR MEASURING SURFACE PLASMON RESONANCE

(75) Inventor: Hirohiko Tsuzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1512 days.

(21) Appl. No.: 11/085,071

(22) Filed: Mar. 22, 2005

(65) Prior Publication Data

US 2005/0216205 A1 Sep. 29, 2005

(30) Foreign Application Priority Data

Mar. 26, 2004 (JP) .............................. 2004-093051
Mar. 26, 2004 (JP) .............................. 2004-093052

(51) Int. Cl.
G01N 21/00 (2006.01)
G01N 21/55 (2006.01)
G01N 33/53 (2006.01)
G01N 35/08 (2006.01)

(52) U.S. Cl. ................. 436/164; 422/82.06; 422/82.07; 422/82.08; 422/82.09; 422/82.11; 422/82.05; 435/7.1; 435/287.2; 205/777.5; 356/300; 356/301; 356/445; 436/52

(58) Field of Classification Search ..................... 435/6, 435/52; 205/777.5; 356/445
See application file for complete search history.

(56) References Cited

U.S. PATENT DOCUMENTS 5,629,213 A  5/1997 Kornguth et al.
5,653,862 A * 8/1997 Parris ....................... 205/777.5
6,730,487 B2 * 5/2004 Latov et al. ................... 435/7.1

FOREIGN PATENT DOCUMENTS

JP  2001-330560  * 11/2001

* cited by examiner

*Primary Examiner*—Jill Warden
*Assistant Examiner*—Neil Turk
(74) *Attorney, Agent, or Firm*—Sughrue Mion, PLLC

(57) ABSTRACT

An object of the present invention is to suppress variations in measurement values when measuring a specific binding reaction between a physiologically active substance and a tested substance using a surface plasmon resonance measurement device, so that binding detection data with high reliability is obtained. The present invention provides a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein a major axis of the metal film is 0.1 μm or more and 100 μm or less; a molecule interacting with an analyzed molecule is immobilized on the surface of the metal film; the distance between metal films is 200 μm or more and 10 mm or less; and the molecule interacting with the analyzed molecule is not immobilized on any parts other than the metal films.

9 Claims, 3 Drawing Sheets

METHOD FOR MEASURING SURFACE PLASMON RESONANCE

TECHNICAL FIELD

The present invention relates to a method for measuring surface plasmon resonance, a surface plasmon resonance measurement device, and a method for detecting or measuring a substance interacting with a physiologically active substance using the above method.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules. An example of a surface plasmon resonance measurement device is the device described in Japanese Patent Laid-Open (Kokai) No. 2001-330560.

When a specific binding reaction between a physiologically active substance and a test substance is measured, the binding reaction is generally measured by: connecting in series a reference cell, to which a physiologically active substance interacting with a test substance does not bind, with a detection cell, to which a physiologically active substance interacting with a test substance binds; placing the connected cells in a flow channel system; and feeding a liquid through the reference cell and the detection cell, so as to carry out the measurement of the binding reaction. During the measurement, the liquid contained in the above flow channel system is exchanged from a reference liquid containing no test substance to be measured to a sample liquid containing a test substance to be measured, so as to cause the binding reaction between the physiologically active substance and the test substance to be initiated, and to measure a change in signals due to a lapse of time. However, this measurement method is problematic in terms of the noise width of the change in signals of the reference cell during measurement and in terms of base line fluctuation. The measurement values fluctuate, and thus it has been difficult to obtain binding detection data with high reliability.

DISCLOSURE OF THE INVENTION

It is an object of the present invention is to solve the aforementioned problems of the prior art techniques. Namely, an object of the present invention is to suppress variations in measurement values when measuring a specific binding reaction between a physiologically active substance and a tested substance using a surface plasmon resonance measurement device, so that binding detection data with high reliability is obtained.

As a result of the present inventor's research and analysis to solve the above object, it was found that the aforementioned object can be achieved by setting a major axis of a metal film to which a molecule interacting with an analyzed molecule is immobilized to be 0.1 μm or more and 100 μm or less while setting the distance between metal films to be 200 μm or more and 10 mm or less, when measuring a change in surface plasmon resonance by replacing a liquid in a flow channel system using a surface plasmon resonance measurement device. The present invention has been completed based on this understanding.

The present invention provides a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein a major axis of the metal film is 0.1 μm or more and 100 μm or less; a molecule interacting with an analyzed molecule is immobilized on the surface of the metal film; the distance between metal films is 200 μm or more and 10 mm or less; and the molecule interacting with the analyzed molecule is not immobilized on any parts other than the metal films.

The present invention further provides a method for measuring a change in surface plasmon resonance, which comprises: using a surface plasmon resonance measurement device comprising a metal film, a light source for generating a light beam, an optical system for allowing the above light beam to enter so that total reflection conditions can be obtained at the interface of the metal film and so that various incidence angles can be included, a flow channel system comprising a cell formed on the above metal film, and a light-detecting means for detecting the state of surface plasmon resonance by measuring the intensity of the light beam totally reflected at the above interface, and exchanging the liquid contained in the above flow channel system, wherein a major axis of the metal film is 0.1 μm or more and 100 μm or less; a molecule interacting with an analyzed molecule is immobilized on the surface of the metal film; the distance between metal films is 200 μm or more and 10 mm or less; and the molecule interacting with the analyzed molecule is not immobilized on any parts other than the metal films.

Preferably in the above, a change in surface plasmon resonance is measured in a state where the flow of the liquid has been stopped, after the liquid contained in the above flow channel system has been exchanged.

The present invention also provides a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein, on the metal surface, there is provided a region [region (a)] having a major axis of 0.1 μm or more and 100 μm or less where a molecule interacting with an analyzed molecule is immobilized; around region (a) which is located in areas separated from the periphery of region (a) by 200 μm or more and 10 mm or less, there is also provided a region [region (b)] where the molecule interacting with the analyzed molecule is not immobilized; and a change in surface plasmon resonance is measured in a state where the flow of the liquid has been stopped, after the liquid contained in the above flow channel system has been exchanged.

The present invention further provides a method for measuring a change in surface plasmon resonance, which comprises: using a surface plasmon resonance measurement device comprising a metal film, a light source for generating a light beam, an optical system for allowing the above light beam to enter so that total reflection conditions can be obtained at the interface of the metal film and so that various incidence angles can be included, a flow channel system comprising a cell formed on the above metal film, and a light-detecting means for detecting the state of surface plasmon resonance by measuring the intensity of the light beam totally reflected at the above interface, and exchanging the liquid contained in the above flow channel system, wherein, on the metal surface, there is provided a region [region (a)] having a major axis of 0.1 μm or more and 100 μm or less where a molecule interacting with an analyzed molecule is immobilized; around region (a) which is located in areas separated from the periphery of region (a) by 200 μm or more and 10 mm or less, there is also provided a region [region (b)] where the molecule interacting with the analyzed molecule is not immobilized; and a change in surface plasmon resonance is measured in a state where the flow of the liquid has been stopped, after the liquid contained in the above flow channel system has been exchanged.

Preferably, the ratio (Ve/Vs) of the amount of a liquid exchanged (Ve ml) in a single measurement to the volume of the above cell (Vs ml) is between 1 and 100, and more preferably the ratio (Ve/Vs) is between 1 and 50.

Preferably, the time required for the exchange of the liquid contained in the above flow channel system is between 0.01 second and 100 seconds.

Preferably, the major axis of the region of a metal film where a molecule interacting with an analyzed molecule is immobilized is 1 μm or more and 50 μm or less.

Preferably, in areas separated from the periphery of region [region (a)] where a molecule interacting with an analyzed molecule is immobilized by 200 μm or more and 1 mm or less, there is provided a region [region (b)] where the molecule interacting with the analyzed molecule is not immobilized.

In another aspect, the present invention provides a method for detecting or measuring a substance interacting with a physiologically active substance, which comprises steps of: using at least a cell, to the surface of which a physiologically active substance binds by covalent bonding; allowing a sample liquid containing a test substance to be measured to come into contact with the above cell; and measuring a change in surface plasmon resonance by the aforementioned method of the present invention.

In another aspect, the present invention provides a surface plasmon resonance measurement device comprising a flow channel system having a cell formed on a metal film and a light-detecting means for detecting the state of surface plasmon resonance by measuring the intensity of a light beam totally reflected on the metal film, wherein a major axis of the metal film is 0.1 μm or more and 100 μm or less; a molecule interacting with an analyzed molecule is immobilized on the surface of the metal film; the distance between metal films is 200 μm or more and 10 mm or less; and the molecule interacting with the analyzed molecule is not immobilized on any parts other than the metal films.

Preferably, the major axis of the region of a metal film where a molecule interacting with an analyzed molecule is immobilized is 1 μm or more and 50 μm or less.

BRIEF DESCRIPTION OF THE INVENTION

BEST MODE FOR CARRYING OUT THE INVENTION

Figure 1:
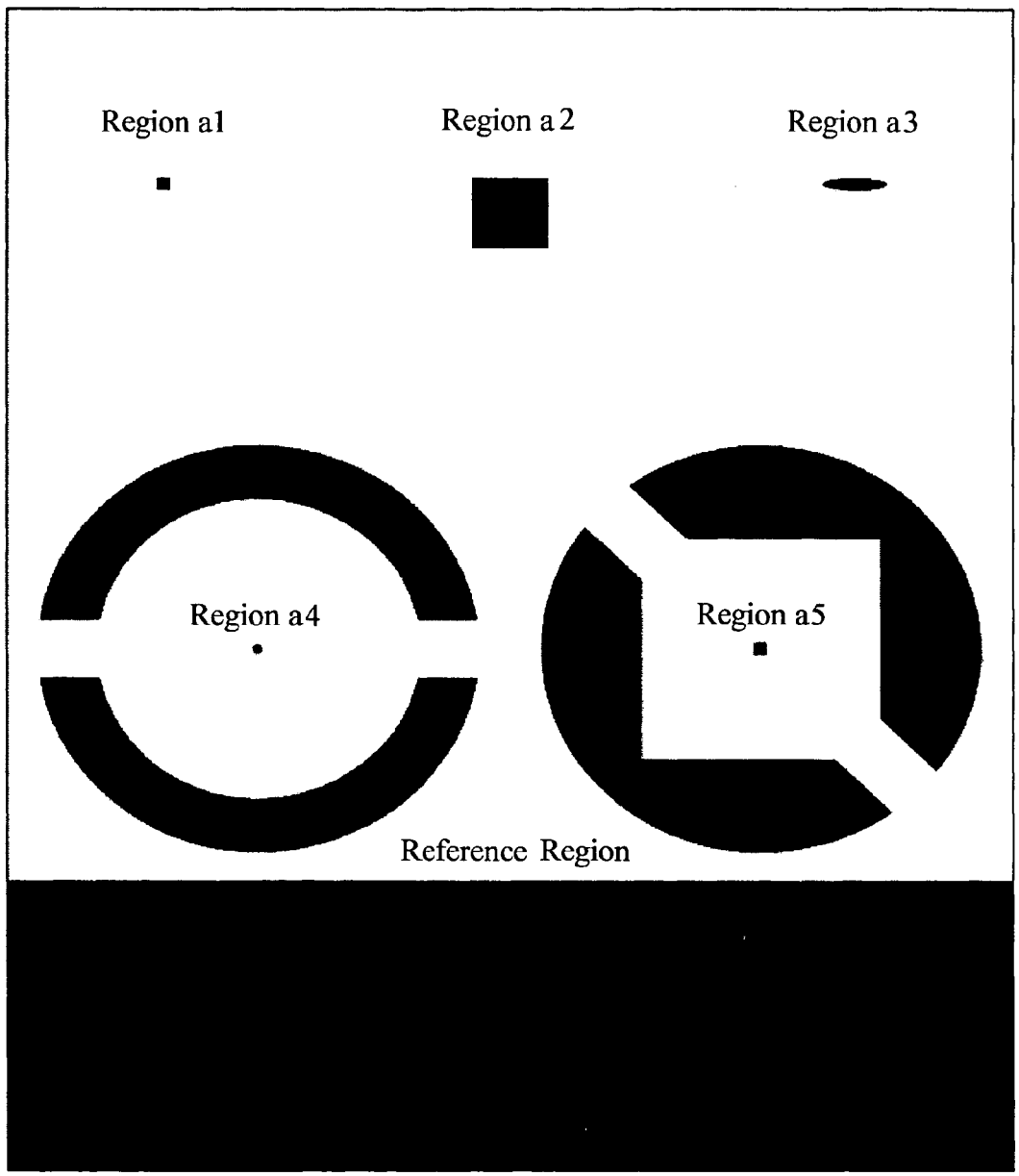
FIG. 1 shows metal film regions in a measurement chip used in an example.

The embodiments of the present invention will be described below.

The first measurement method of the present invention relates to a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein a major axis of the metal film is 0.1 μm or more and 100 μm or less; a molecule interacting with an analyzed molecule is immobilized on the surface of the metal film; the distance between metal films is 200 μm or more and 10 mm or less; and the molecule interacting with the analyzed molecule is not immobilized on any parts other than the metal films.

The second measurement method of the present invention relates a method for measuring a change in surface plasmon resonance, which comprises: using a surface plasmon resonance measurement device comprising a flow channel system having a cell formed on a metal film and a light-detecting means for detecting the state of surface plasmon resonance by measuring the intensity of a light beam totally reflected on the metal film; and exchanging the liquid contained in the above flow channel system, wherein, on the metal surface, there is provided a region [region (a)] having a major axis of 0.1 μm or more and 100 μm or less where a molecule interacting with an analyzed molecule is immobilized; around region (a) which is located in areas separated from the periphery of region (a) by 200 μm or more and 10 mm or less, there is also provided a region [region (b)] where the molecule interacting with the analyzed molecule is not immobilized; and a change in surface plasmon resonance is measured in a state where the flow of the liquid has been stopped, after the liquid contained in the above flow channel system has been exchanged.

An analyzed molecule is adsorbed onto a molecule interacting with the analyzed molecule that is immobilized on the metal surface over time.

$$d\theta/dt = k_a \cdot c_s \cdot (1-\theta) - k_d \cdot \theta \quad (1)$$

where $\theta$ is the ratio of adsorption (=adsorption amount/saturated adsorption amount), $k_a$ is the adsorption rate coefficient, $k_d$ is the separation rate, and $c_s$ is the concentration of the analyzed molecule near the metal surface.

In an ideal condition where the metal surface could be constantly supplied with a fresh fluid substitution, $c_s$ would be constant and it would be possible to determine $k_a$, $k_d$ by solving simple differential equations based on measurement results.

However, the flow on the metal surface is extremely slow, and so it would be necessary to cause an analyzed-molecule solution to flow at high speed if $c_s$ were to be maintained as a constant. Meanwhile, surface plasmon involves fluctuations in signals caused by disturbances in the flow on the metal surface, and a large quantity of the analyzed molecule would be required if the rate of the flow were to be increased. For these reasons, it is actually impossible to make $c_s$ constant.

When $c_s$ is not constant, the change in concentration due to the adsorption or separation of the analyzed molecule is represented by a function that varies due to the diffusion of the analyzed molecule from offshore areas. The diffusion is represented by the following equation (2):

$$\partial c/\partial t = D \cdot \partial^2 c/\partial x^2 \quad (2)$$

where x is the distance from the metal surface, D is the diffusion coefficient of the analyzed molecule, and c is the concentration of the analyzed molecule, and where when $x=0$, $c=c_s$.

At the periphery of the portion [region (a)] where a molecule interacting with the analyzed molecule is immobilized, the analyzed molecule is fed from above the portion [region (b)] where the interacting molecule is not immobilized. Therefore, at the periphery portion, the rate of diffusion is substantially increased. Thus, as the distance between the center of region (a) and region (b) decreases, the rate of feeding of the analyzed molecule increases in the entire region (a), such that the adsorption and separation substantially follow Langmuir's adsorption equation.

Further, the incident light during the surface plasmon measurement produces a blurring at the reflecting surface. As a result, if region a becomes significantly smaller than the light-blurred region, the region where there is an absence of interaction with the analyzed molecule increases in the measured area, leading to the problem that the signal due to the adsorption or separation of the analyzed molecule becomes smaller.

The major axis of region (a) is 0.1 μm or more and 100 μm or less, and preferably 1 μm or more and 100 μm or less. More preferably, it is 1 μm or more and 50 μm or less, and yet more preferably it is 5 μm or more and 50 μm or less. Still preferably, it is 5 μm or more and 30 μm or less, and particularly preferably it is 10 μm or more and 30 μm or less.

Preferably, region (b) is a region in areas separated from the periphery of region (a) by 200 μm or more and 1 mm or less where the molecule interacting with the analyzed molecule is not immobilized. Preferably, the above distance is ten or more times larger than the major axis of region (a).

The ratio (Ve/Vs) of the amount of a liquid exchanged (Ve ml) in a single measurement to the volume (Vs ml) of the aforementioned cell is preferably between 1 and 100. Ve/Vs is more preferably between 1 and 50, and particularly preferably between 1 and 20. The volume (Vs ml) of a cell used in measurement is not particularly limited. It is preferably between $1 \times 10^{-6}$ and 1.0 ml, and particularly preferably between $1 \times 10^{-5}$ and $1 \times 10^{-1}$ ml.

In the measurement method of the present invention, a change in surface plasmon resonance is preferably measured in a state where the flow of a liquid has been stopped, after the liquid contained in the above flow channel system has been exchanged. The time of the stop of the flow of the liquid is not particularly limited. For example, it may be between 1 second and 30 minutes, preferably between 10 seconds and 20 minutes, and more preferably between 1 minute and 20 minutes.

In the present invention, preferably, the liquid contained in a flow channel system is exchanged from a reference liquid containing no test substance to be measured to a sample liquid containing a test substance to be measured, and thereafter, a change in surface plasmon resonance can be measured in a state where the flow of the sample liquid has been stopped.

The period of time necessary for exchanging the liquid is preferably between 0.01 second and 100 seconds, more preferably between 0.1 second and 10 seconds.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light. The surface plasmon resonance measurement device used in the present invention will be described below.

The surface plasmon resonance measurement device is a device for analyzing the properties of a substance to be measured using a phenomenon whereby a surface plasmon is excited with a lightwave. The surface plasmon resonance measurement device used in the present invention comprises a metal film, a light source for generating a light beam, an optical system for allowing the above light beam to enter such that total reflection conditions can be obtained at the interface of the metal film and that components at various incident angles can be contained, and a light-detecting means for detecting the state of surface plasmon resonance by measuring the intensity of the light beam totally reflected at the above interface.

In the present invention, more specifically, a surface plasmon resonance measurement device shown in FIGS. 1 to 32 of Japanese Patent Laid-Open No. 2001-330560, and a surface plasmon resonance device shown in FIGS. 1 to 15 of Japanese Patent Laid-Open No. 2002-296177, can be preferably used. All of the contents as disclosed in Japanese Patent Laid-Open Nos. 2001-330560 and 2002-296177 cited in the present specification are incorporated herein by reference as a part of the disclosure of this specification.

For example, the surface plasmon resonance measurement device described in Japanese Patent Laid-Open No. 2001-330560 is characterized in that it comprises: a dielectric block; a thin metal film formed on a face of the dielectric block; multiple measurement units comprising a sample-retaining mechanism for retaining a sample on the surface of the thin film; a supporting medium for supporting the multiple measurement units; a light source for generating a light beam; an optical system for allowing the above light beam to enter the dielectric block at various angles so that total reflection conditions can be obtained at the interface between the dielectric block and the metal film; a light-detecting means for measuring the intensity of the light beam totally reflected at the above interface and detecting the state of attenuated total reflection caused by surface plasmon resonance; and a driving means for making the above supporting medium, the above optical system and the above light-detecting means move relative to one another, and successively placing each of the above multiple measurement units in a certain position appropriate to the above optical system and the above light-detecting means, so that the above total reflection conditions and various incident angles can be obtained with respect to each dielectric block of the above multiple measurement units.

It is to be noted that in the above measurement device, the above optical system and light-detecting means are kept in a resting state and the above driving means makes the above supporting medium move.

In such a case, the above supporting medium is desirably a turntable for supporting the above multiple measurement units on a circle centered on a rotation axis, and the above driving means is desirably a means for intermittently rotating this turntable. In this case, a medium for supporting the above multiple measurement units that are linearly arranged in a line may be used as the above supporting medium, and a means that makes such a supporting medium move linearly in an intermittent fashion in the direction in which the above multiple measurement units are arranged may be applied as the above driving means.

Otherwise, on the contrary, it may also be possible that the above supporting medium be retained in a resting state and that the above driving means makes the above optical system and light-detecting means move.

In such a case, the above supporting medium is desirably a medium for supporting the above multiple measurement units on a circle, and the above driving means is desirably a means for intermittently rotating the above optical system and light-detecting means along the multiple measurement units supported by the above supporting medium. In this case, a medium for supporting the above multiple measurement units that are linearly arranged in a line may be used as the above supporting medium, and a means that makes the above optical system and light-detecting means move linearly in an intermittent fashion along the multiple measurement units supported by the above supporting medium may be applied as the above driving means.

Otherwise, when the above driving means has a rolling bearing that supports a rotation axis, the driving means is desirably configured such that after the rotation axis has been rotated to a certain direction and a series of measurements for the above multiple measurement units has been terminated, the above rotation axis is equivalently rotated to the opposite direction, and then it is rotated again to the same above direction for the next series of measurements.

In addition, the above-described measurement device is desirably configured such that the above multiple measurement units are connected in a line with a connecting member so as to constitute a unit connected body and that the above supporting medium supports the unit connected body.

Moreover, in the above-described measurement device, it is desirable to establish a means for automatically feeding a given sample to each sample-retaining mechanism of the multiple measurement units supported by the above supporting medium.

Furthermore, in the above-described measurement device, it is desirable that the dielectric block of the above measurement unit be immobilized to the above supporting medium, that a thin film layer and a sample-retaining mechanism of the measurement unit be unified so as to constitute a measurement chip, and that the measurement chip be formed such that it is exchangeable with respect to the above dielectric block.

When such a measurement chip is applied, it is desirable to establish a cassette for accommodating a multiple number of the measurement chips and a chip-supplying means for successively taking a measurement chip out of the cassette and supplying it in a state in which it is connected to the above dielectric block.

Otherwise, it may also be possible to unify the dielectric block of the measurement unit, the thin film layer and the sample-retaining mechanism, so as to constitute a measurement chip, and it may also be possible for this measurement chip to be formed such that it is exchangeable with respect to the above supporting medium.

When a measurement chip has such a structure, it is desirable to establish a cassette for accommodating a multiple number of measurement chips and a chip-supplying means for successively taking a measurement chip out of the cassette and supplying it in a state in which it is supported by the supporting medium.

The above optical system is desirably configured such that it makes a light beam enter the dielectric block in a state of convergent light or divergent light. Moreover, the above light-detecting means is desirably configured such that it detects the position of a dark line generated due to attenuated total reflection, which exists in the totally reflected light beam.

Furthermore, the above optical system is desirably configured such that it makes a light beam enter the above interface in a defocused state. In this case, the beam diameter of the light beam at the above interface in a direction wherein the above supporting medium moves is desirably ten times or greater the mechanical positioning precision of the above supporting medium.

Still further, the above-described measurement device is desirably configured such that the measurement unit is supported on the upper side of the above supporting medium, such that the above light source is placed so as to project the above light beam from a position above the above supporting medium to downwards, and such that the above optical system comprises a reflecting member for reflecting upwards the above light beam projected to downwards as described above and making it proceed towards the above interface.

Still further, the above-described measurement device is desirably configured such that the above measurement unit is supported on the upper side of the above supporting medium, such that the above optical system is constituted so as to make the above light beam enter the above interface from the downside thereof, and such that the above light-detecting means is placed in a position above the above supporting medium with a light-detecting plane thereof facing downwards, as well as comprising a reflecting member for reflecting upwards the totally reflected light beam at the above interface and making it proceed towards the above light-detecting means.

What is more, the above-described measurement device desirably comprises a temperature-controlling means for maintaining the temperature of the above measurement unit before and/or after being supported by the above supporting medium at a predetermined temperature.

Moreover, the above-described measurement device desirably comprises a means for stirring the sample stored in the sample-retaining mechanism of the measurement unit supported by the above supporting medium before detecting the state of attenuated total reflection as mentioned above.

Furthermore, in the above-described measurement device, it is desirable to establish in at least one of the multiple measurement units supported by the above supporting medium a standard solution-supplying means for supplying a standard solution having optical properties associated with the optical properties of the above sample, as well as a correcting means for correcting data regarding the above attenuated total reflection state of the sample based on the data regarding the above attenuated total reflection state of the above standard solution.

In such a case, if the sample is obtained by dissolving a test substance in a solvent, it is desirable that the above standard solution-supplying means be a means for supplying the above solvent as a standard solution.

Still further, the above measurement device desirably comprises: a mark for indicating individual recognition information; a reading means for reading the above mark from the measurement unit used in measurement; an inputting means for inputting sample information regarding the sample supplied to the measurement unit; a displaying means for displaying measurement results; and a controlling means connected to the above displaying means, inputting means and reading means, which stores the above individual recognition information and sample information of each measurement unit while associating them with each other, as well as making the above displaying means display the measurement results of the sample retained in a certain measurement unit while associating them with the above individual recognition information and sample information of each measurement unit.

When a substance interacting with a physiologically active substance is detected or measured using the above-described measurement device, a state of attenuated total reflection is detected in a sample contained in one of the above measurement units, and thereafter, the above supporting medium, optical system and light-detecting means are moved relative to one another, so that a state of attenuated total reflection is detected in a sample contained in another measurement unit. Thereafter, the above supporting medium, optical system and light-detecting means are again moved relative to one another, so that a state of attenuated total reflection is detected again the sample contained in the above one measurement unit, thereby completing the measurement.

The measurement chip used in the present invention is used for the surface plasmon resonance measurement device having a structure described herein, and is composed of a metal film.

A metal constituting the metal film is not particularly limited, as long as surface plasmon resonance is generated. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

Preferably, the metal film has a functional group capable of immobilizing a physiologically active substance on the outermost surface of the substrate. The term "the outermost surface of the substrate" is used to mean "the surface, which is farthest from the substrate".

Examples of a preferred functional group may include —OH, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

Examples of the method of introducing such a functional group include a method which involves applying a polymer containing a precursor of such a functional group on a metal surface or metal film, and then generating the functional group from the precursor located on the outermost surface by chemical treatment.

In the measurement chip obtained as mentioned above, a physiologically active substance is covalently bound thereto via the above functional group, so that the physiologically active substance can be immobilized on the metal film.

A physiologically active substance immobilized on the surface for the measurment chip of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgQ, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme, or nucleic acid, an amino group, thiol group or the like of the physiologically active substance is covalently bound to a functional group located on a metal surface, so that the physiologically active substance can be immobilized on the metal surface.

A measurement chip to which a physiologically active substance is immobilized as described above can be used to detect and/or measure a substance which interacts with the physiologically active substance.

Namely, the present invention provides a method for detecting or measuring a substance interacting with a physiologically active substance, which comprises measuring a change in surface plasmon resonance by using a surface plasmon resonance measurement device comprising a flow channel system having a cell formed on a metal film and a light-detecting means for detecting the state of surface plasmon resonance by measuring the intensity of a light beam totally reflected on the metal film, and exchanging the liquid contained in the above flow channel system, under conditions where a major axis of the metal film is 0.1 μm or more and 100 μm or less; a molecule interacting with an analyzed molecule is immobilized on the surface of the metal film; the distance between metal films is 200 μm or more and 10 mm or less; and the molecule interacting with the analyzed molecule is not immobilized on any parts other than the metal films.

As a test substance, a sample containing a substance interacting with the aforementioned physiologically active substance can be used, for example.

EXAMPLES

The following examples can be performed using the SPR imager manufactured by GWC Instruments.

Example A-1

Preparation of a Dextran Measurement Chip

A metal film of gold with a thickness of 50 nm was evaporated on a glass plate (BSC7 by Hoya Corporation), which had been optically polished to a thickness of 0.3 mm, only in regions a1 to a5 and a reference region as shown blacked out in FIG. 1. After treating in a Model-208 UV-ozone cleaning system (TECHNOVISION INC.) for 30 minutes, 5.0 mM solution of 11-hydroxy-1-undecanethiol in ethanol/water (80/20) was added such that the solution came into contact with the metal film. The surface treatment was continued for 18 hours at 25° C. Thereafter, washing was performed 5 times with ethanol, once with an ethanol/water mixture solvent, and 5 times with water. In the figure, region a3 (invention) is an ellipse with a major axis of 100 μm and a minor axis of 20 μm; a region a1 (invention) is a square with sides of 20 μm; region a2 (comparative example) is a square with sides of 120 μm, that are separated from any of the gold films by 200 μm or more. Region a4 (invention) is a circle with a diameter of 15 μm with a gold film partially located 250 μm away from the periphery thereof, and region a5 (comparative example) is a square with sides of 20 μm with a gold film partially located 150 μm from the periphery thereof. The reference region is a rectangle with lengths of 1600 μm and widths of 500 μm.

Then, 2-butanone solution of polystyrene is applied only to the reference region, resulting in a dry film thickness of 10 nm, so that the molecule interacting with the analyzed molecule as well as the analyzed molecule would not bind to the gold film. The thus prepared chip with gold partially attached thereto is then immersed in an ethanol solution of 11-hydroxy-1-undecanethiol, such that only reference regions a1 to a5 where gold has been exposed are coated with 11-hydroxy-1-undecanethiol. The coated surfaces are brought into contact with a 10 weight % epichlorohydrin solution (solvent: a 1:1 mixture solution of 0.4M sodium hydroxide and diethylene glycol dimethyl ether), and they were reacted in a shaking incubator at 25° C. for 4 hours. The surfaces were washed twice with ethanol and 5 times with water.

4.5 ml of 1M sodium hydroxide was further added to 40.5 ml of a 25 weight % aqueous solution of dextran (T500, Pharmacia), and the solution was brought into contact with the epichlorohydrin-treated surfaces. Incubation was then performed in a shaking incubator at 25° C. for 20 hours. The surfaces were washed 10 times with water of 50° C. Thereafter, a mixture in which 3.5 g of bromoacetic acid had been dissolved in 27 g of a 2M sodium hydroxide solution was brought into contact with the aforementioned dextran-treated surfaces, and then incubation was carried out in a shaking incubator at 28° C. for 16 hours. The surfaces were washed with water, and the above-described procedure was repeated once.

Through these operations, only the gold film surface can be modified with the molecule interacting with the analyzed molecule.

Example A-2

Preparation of a Trypsin-Immobilized Chip

After solutions in the above-described dextran measurement chip were removed, the chip was immersed in a mixture solution of 200 mM EDC (N-ethyl-N'-(3-dimethylaminopropyl)carbodiimide hydrochloride) and 50 mM NHS (N-hydroxysuccinimide) and was then allowed to stand for 10 minutes. After the mixture solution was removed, the chip was washed 3 times with water and 3 times with a buffer 1 (10 mM of HEPES (N-2-hydroxyethyl piperazine-N'-2-ethane sulfonic acid), 150 mM NaCl, and 10 mM $CaCl_2$). Thereafter, the chip was immersed in a trypsin solution (dissolved in buffer 1 to 1 mg/ml) and then allowed to stand for 30 minutes, thereby immobilizing trypsin. The immersion liquid was then replaced with a 1M ethanolamine solution, and the chip was allowed to stand for 10 minutes. Further, the chip was washed 10 times with buffer 1. In this way, trypsin was immobilized on only the gold film portion, as shown in FIG. 1.

The chip with trypsin thus immobilized thereon was then immersed in 1M ethanolamine solution for 10 minutes and washed 10 times with buffer 1, thereby preparing a trypsin-immobilized chip.

Example A-3

Evaluation of Leupeptin Binding Capacity

The thus obtained trypsin-immobilized chip is set on a surface plasmon measurement device. A sucrose solution with a known refractive index is delivered, and an analytical curve relating the output of the surface plasmon device to the refractive index is prepared. A change in the refractive index in the vicinity of the metal surface is linearly related to the amount of adsorption of the analyzed molecule (leupeptin). Using the analytical curve, the output value of the surface plasmon device is calibrated with respect to the refractive index, thereby obtaining a surface plasmon signal.

The fluid channel system is filled with a buffer 2 (10 mM HEPES and 150 mM NaCl). While measuring a signal change (R) at the center of the regions a1 to a5 with reference to the center of the reference portion, a leupeptin solution (dissolved in buffer 2 to 1 g/ml) is delivered until the fluid is substituted, whereupon the delivery of the solution is immediately terminated. Then, a leupeptin solution (dissolved in buffer 2 to 100 μg/ml) for measuring the saturated adsorption amount is delivered and the maximum adsorption signal amount (Rmax) is determined. Using the R/Rmax as the adsorption amount θ, $k_a$ and $k_d$ are determined by fitting with respect to time in accordance with Langmuir's equation. A similar measurement is repeated 10 times, and the logarithm of $k_a$ and $k_d$ calculated in each measurement is obtained. The degree of dispersion in the measurement result is evaluated using the standard deviation/mean value×100% as an index. Good results of less than 10% are obtained in the regions a1, a3, and a4 of the present invention, whereas in the regions a2 and a5 of the comparative examples, the results are 100% or more, suggesting a poor measurement accuracy.

Example B-1

Preparation of a Dextran Measurement Chip

A metal film of gold with a thickness of 50 nm was evaporated on a glass plate (BSC7 by Hoya Corporation) that had been optically polished to a thickness of 0.3 mm. After treatment in a Model-208 UV-ozone cleaning system (TECHNO-VISION INC.) for 30 minutes, 5.0 mM solution of 11-hydroxy-1-undecanethiol in ethanol/water (80/20) was added such that the solution came into contact with the metal film. Thereafter, washing was performed 5 times with ethanol, once with an ethanol/water mixture solvent, and 5 times with water.

Then, the surface coated with 11-hydroxy-1-undecanethiol was brought into contact with 10 weight % epichlorohydrin solution (solvent: a 1:1 mixture solution of 0.4M sodium hydroxide and diethylene glycol dimethyl ether) and reacted in a shaking incubator at 25° C. for 4 hours. The surface was then washed twice with ethanol and 5 times with water.

4.5 ml of 1M sodium hydroxide was then added to 40.5 ml of 25 weight % aqueous solution of dextran (T500, Pharmacia), and the solution was brought into contact with the epichlorohydrin-treated surface. The chip was incubated in a shaking incubator at 25° C. for 20 hours. The surface is then washed 10 times with water of 50° C.

A mixture in which 3.5 g of bromoacetic acid had been dissolved in 27 g of a 2M sodium hydroxide solution was brought into contact with the dextran-treated surface. After incubation in a shaking incubator at 28° C. for 16 hours, the surface was washed with water. Thereafter, the above-described procedure was repeated once.

Example B-2

Preparation of a Trypsin-Immobilized Chip

After solutions in the above dextran measurement chip were removed, the chip was immersed in a mixture solution of 200 mM EDC (N-ethyl-N'-(3-dimethylaminopropyl)carbodiimide hydrochloride) and 50 mM NHS (N-hydroxysuccinimide) and was then allowed to stand for 10 minutes. After the mixture solution was removed, the chip was washed 3 times with water and 3 times with buffer 1 (10 mM of HEPES(N-2-hydroxyethyl piperazine N'-2-ethane sulfonic acid), 150 mM NaCl, and 10 mM $CaCl_2$).

Figure 2:
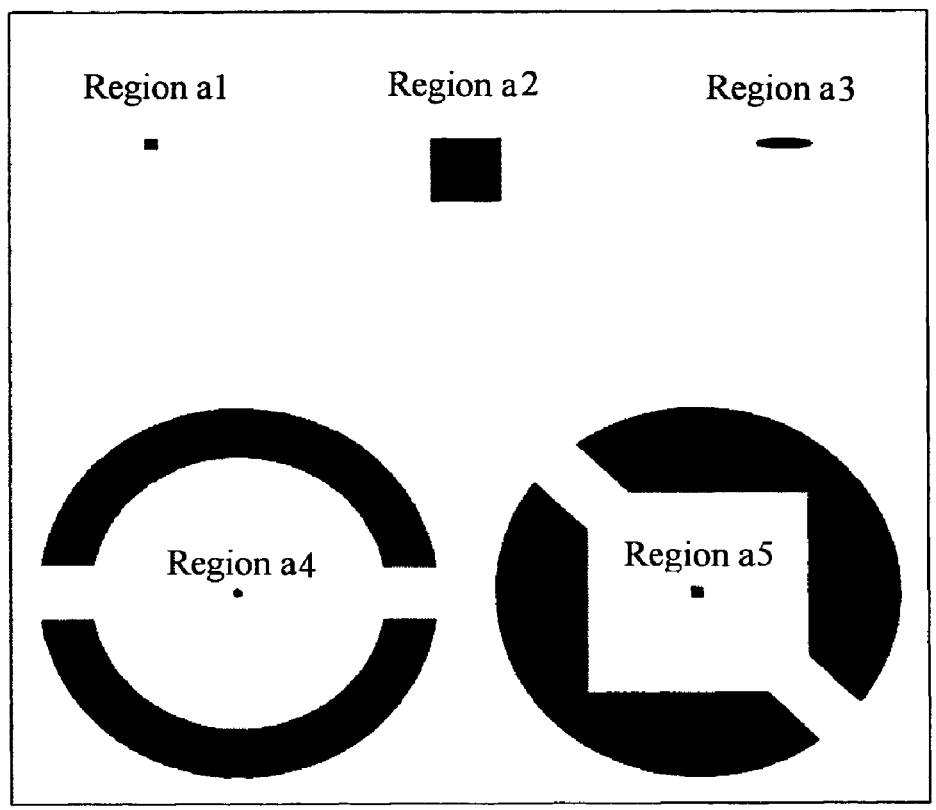
FIG. 2 shows a region including an opening in a SILPOT™ from Dow Corning used in an example.
Figure 3:
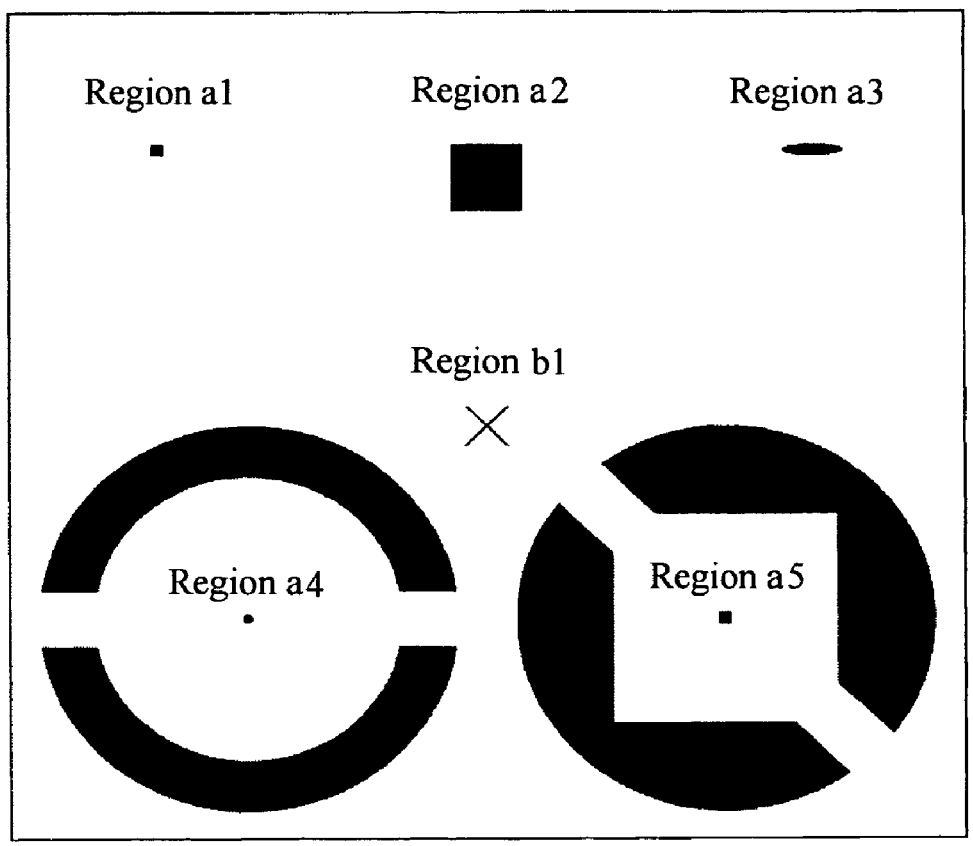
FIG. 3 shows a trypsin-immobilized region in a trypsin-immobilized chip.

Then, a mask with a thickness of 100 μm made from SILPOT™ 184 from Dow Corning with an opening at a portion as shown in FIG. 2 was pressed against the chip, and a trypsin solution (dissolved in buffer 1 to 1 mg/ml) was put in the opening. The chip was then allowed to stand for 30 minutes, thereby immobilizing trypsin. The inside of the chip was then replaced with a 1M ethanolamine solution, and the chip was allowed to stand for 10 minutes. The insides of the opening are washed 10 times with buffer 1. Thus, trypsin can be immobilized as shown in FIG. 2. Region a3 (invention) is an ellipse with a major axis of 100 μm and a minor axis of 20 μm, region a1 (invention) is a square with sides of 20 μm, and region a2 (comparative example) is a square with sides of 120 μm, which are separated from any of the trypsin-immobilized lower portions by 200 μm or more. Region a4 (invention) is a circle with a diameter of 15 μm, with trypsin partially immobilized 250 μm from the periphery thereof. Region a5 (comparative example) is a square with sides of 20 μm with trypsin partially immobilized 150 μm from the periphery thereof.

The above trypsin-immobilized chip is immersed in 1M ethanolamine solution for 10 minutes and then washed 10 times with buffer 1, thereby preparing a trypsin-immobilized chip.

Example B-3

Evaluation of Leupeptin Binding Capacity

The thus obtained trypsin-immobilized chip is set on a surface plasmon measurement device. A sucrose solution with a known refractive index is delivered, and an analytical curve relating the output of the surface plasmon device to the refractive index is prepared. A change in the refractive index in the vicinity of the metal surface is linearly related to the amount of adsorption of the analyzed molecule (leupeptin). Using the analytical curve, the output value of the surface plasmon device is calibrated with respect to the refractive index, thereby obtaining a surface plasmon signal.

The fluid channel system is then filled with a buffer 2 (10 mM HEPES and 150 mM NaCl). While measuring a signal change (R) at the center of the regions a1 to a5 with reference to region b1 that is the center of the area indicated by x in FIG. 3, which is separated from any of the trypsin-immobilized portions by 200 μm or more, a leupeptin solution (dissolved in buffer 2 to 1 μg/ml) is delivered into the fluid channel system until the solution is substituted, whereupon the delivery is immediately terminated. Thereafter, a leupeptin solution (dissolved in buffer 2 to 100 μg/ml) for measuring the saturated adsorption amount is delivered, and the maximum adsorption signal amount (Rmax) is determined. Using R/Rmax as the adsorption amount θ, $k_a$ and $k_d$ are determined by fitting with respect to time in accordance with Langmuir's adsorption equation. A similar measurement is repeated 10 times, and the logarithm of $k_a$ and $k_d$ calculated in each measurement is determined. Using the standard deviation/mean value×100% as an index, the degree of dispersion of the measurement results is evaluated. Good results of less than 10% are obtained in regions a1, a3, and a4 of the present invention, whereas in regions a2 and a5, which are comparative examples, the results are 100% or more, suggesting a poor measurement accuracy.

EFFECT OF THE INVENTION

In accordance with the measuring method and device of the present invention, variations in measurement values can be suppressed and highly reliable binding detection data can be obtained.

The invention claimed is:

1. A method for measuring a change in surface plasmon resonance, which comprises:
   (i) introducing a reference liquid containing no test substance to be measured to a surface plasmon resonance measurement device comprising a flow channel system having a cell formed on a metal film and a light-detecting means for detecting the surface plasmon resonance by measuring the intensity of a light beam totally reflected on the metal film;
   (ii) applying the light beam, and detecting the surface plasmon resonance by measuring the intensity of the light beam totally reflected on the metal film when the reference liquid is contained in the flow channel system;
   (iii) removing the reference liquid and introducing a sample liquid containing a test substance to be measured into the surface plasmon resonance measurement device;
   (iv) applying the light beam, and detecting the surface plasmon resonance by measuring the intensity of the light beam totally reflected on the metal film when the sample liquid is contained in the flow channel system; and
   (v) measuring a change in surface plasmon resonance between the surface plasmon resonance in step (ii) and the surface plasmon resonance in step (iv);
   wherein a major axis of one or more exposed surfaces of the metal film is between 0.1 μm and 100 μm; wherein a molecule interacting with the test substance is immobilized on the one or more exposed surfaces; wherein the distance between the one or more exposed surfaces is between 200 μm and 10 mm; and wherein the molecule interacting with the test substance is not immobilized on any parts other than the one or more exposed surfaces.

2. The method according to claim 1, wherein the surface plasmon resonance measurement device further comprises a light source for generating the light beam and an optical system for allowing the above light beam to enter so that total reflection conditions can be obtained at the interface of the metal film and so that various incidence angles can be included.

3. The measuring method according to claim 1 wherein the change in surface plasmon resonance is measured in a state where the flow of the liquid has been stopped, after the liquid contained in the above flow channel system has been exchanged.

4. The measuring method according to claim 1 wherein the ratio (Ve/Vs) of the amount of a liquid exchanged (Ve ml) in a single measurement to the volume of the above cell (Vs ml) is between 1 and 100.

5. The measuring method according to claim 1 wherein the ratio (Ve/Vs) is between 1 and 50.

6. The measuring method according to claim 1 wherein the time required for the exchange of the liquid contained in the above flow channel system is between 0.01 second and 100 seconds.

7. The measuring method according to claim 1 wherein the major axis of the one or more exposed surfaces of the metal film where a molecule interacting with the test substance is immobilized is between 1 μm and 50 μm.

8. The measuring method according to claim 1 wherein in areas separated from the periphery of the region where the molecule interacting with the test substance is immobilized by a distance of between 200 μm and 1 mm, there is provided a region where the molecule interacting with the test substance is not immobilized.

9. The measuring method according to claim 1 wherein the major axis of one or more exposed surfaces of the metal films is between 10 μm and 30 μm.

* * * * *